United States Patent [19]

Van Heertum et al.

[11] Patent Number: 4,765,826
[45] Date of Patent: Aug. 23, 1988

[54] SUBSTITUTED BENZYLTRIALKYLAMMONIUM SALTS AND THEIR USE AS PLANT GROWTH ENHANCERS

[75] Inventors: John C. Van Heertum, Concord; Maria P. Herrero, Berkeley, both of Calif.

[73] Assignee: The Dow Chemical Company, Midland, Mich.

[21] Appl. No.: 864,679

[22] Filed: May 19, 1986

[51] Int. Cl.$^4$ ............................................. A01N 33/02
[52] U.S. Cl. ..................................... 71/121; 564/287
[58] Field of Search ........................... 71/121; 564/287

[56] References Cited

FOREIGN PATENT DOCUMENTS 0064702 11/1982 European Pat. Off. .
171940 10/1982 Japan .
7009186 12/1986 Netherlands .

OTHER PUBLICATIONS

Aroyan AA Arm. Khim Zh 20(8), 638-48, 1967.

Molina, P. et al., An Univ. Murcia Ciene., volume date 1980-82, 39-40 (1-4) 341-54, 1983.

*Primary Examiner*—Paul J. Killos
*Attorney, Agent, or Firm*—S. Preston Jones; Ronald G. Brookens

[57] ABSTRACT

Compounds are prepared which correspond to the formula

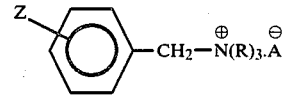

wherein
  Z represents in the 3 or 4 ring position, $C_1$-$C_6$ alkoxy or $C_1$-$C_6$ alkylthio;
  each R independently represents $C_1$-$C_4$ alkyl with the proviso that when Z is a $C_6$ alkoxy or $C_6$ alkylthio, R cannot be $C_4$ alkyl; and
  A represents a non-phytotoxic anion. The compounds have been found to be active plant growth enhancers.

9 Claims, No Drawings

SUBSTITUTED BENZYLTRIALKYLAMMONIUM SALTS AND THEIR USE AS PLANT GROWTH ENHANCERS

BACKGROUND OF THE INVENTION

One active area of agricultural research is devoted to the production of more productive plant life, particularly that plant life usually considered as or associated with food sources or beauty for man. In this research, much effort has been expended in developing means for the regulation of the growth pattern of plant life, particularly as evidenced by the retardation of growth and the enhancement of maturation.

These objectives have been accomplished, in part, by the discovery, development and distribution of various chemical agents which alter or modify the growth characteristics of plants. Documentation of such can be found in Dwarfing Plants With Chemicals, Agricultural Research Service, U.S. Department of Agriculture, January, 1961.

Prior Art

Various ammonium salts have been employed in the control of plant growth. For example, substituted benzyltrialkylammonium salts are taught in Canadian Patent 1,090,799. Substituted benzyltrialkylammonium halides are taught in U.S. Pat. No. 2,722,310. Various quaternary ammonium florides are also taught in U.S. Pat. No. 3,277,118.

The compound N,N,N-triethyl-(4-methoxybenzyl)-ammonium chloride is taught in Chemical Abstracts 64:12596C. However, no utility of this compound is given.

SUMMARY OF THE INVENTION

The present invention is directed to compounds corresponding to the general formula

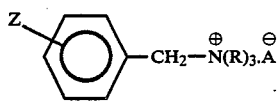

wherein:

Z represents in the 3 or 4 ring position, $C_1$-$C_6$ alkoxy or $C_1$-$C_6$ alkylthio;

each R independently represents $C_1$-$C_4$ alkyl with the proviso that when Z is a $C_6$ alkoxy or $C_6$ alkylthio, R cannot be $C_4$ alkyl; and A represents a non-phytotoxic anion.

The compounds of the above formula have been found to be active in causing an increase in the growth of at least one of corn, wheat and sugar cane plants as indicated by an increase in their dry weight accumulations.

The substituted benzyltrialkylammonium salts of the present invention are solids or oils, soluble in water and appreciably soluble in common organic solvents.

The terms "alkyl," "alkoxy" and "alkylthio" as employed in the present specification and claims designate both straight and branched chained alkyl, alkoxy or alkylthio moieties of the requisite number of carbon atoms.

In the present invention, it is to be noted that all substituent groups are sterically compatible with each other. The term "sterically compatible" is employed to designate substituent groups which are not affected by steric hindrance as defined in "The Condensed Chemical Dictionary," 7th edition, Reinhold Publishing Co., N.Y., page 893 (1966) which definition is a follows:

"steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in "Organic Chemistry" of D. J. Cram and G. Hammon, 2nd edition, McGraw-Hill Book Company, N.Y., page 215 (1964).

The specific anion of the salts of the present invention is not critical. The anion can be any of the anions conventionally employed in plant growth regulators. The only limitation upon the anion chosen is that it be non-phytotoxic to the plants being treated. Representative anions include $Cl^{(-)}$, $Br^{(-)}$, $I^{(-)}$, $SCN^{(-)}$, $CH_3CO_2^{(-)}$, $C_2H_5CO_2^{(-)}$, $\phi SO_3^{(-)}$, $\phi CO_2^{(-)}$, $Cl-\phi-O^{(-)}$, $C_3H_7CO_2^{(-)}$, $SO_4^{(=)}$, $PO_4^{(\equiv)}$, $NO_3^{(-)}$, $ClO_3^{(-)}$, and $N_3^{(-)}$, among others.

The compounds of the present invention can be prepared by the reaction of an appropriate alkoxy or alkylthio substituted benzylhalide (usually a chloride or bromide) and a trialkylamine in the presence of a solvent. The reaction can be characterized as follows:

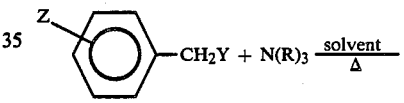

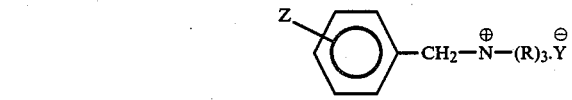

wherein Y is chloro or bromo.

In carrying out this reaction, the reactants and solvent are mixed together in any suitable fashion and the mixture heated at a temperature in the range of from about 65° C. to about 150° C. (dependent upon the reactants) and preferably at the reflux temperature of the mixture. The reactants are maintained under such conditions until the reaction is complete. Since the reaction is rather slow, reaction period of from about 2 hours to 1 week or more are not unusual. The specific time period is dependent upon the specific reactants and solvents employed.

The amount of the reactants to be employed is not critical, some of the product being formed when employing any proportions. The reaction, however, consumes the reactants in the ratio of 1 mole of the benzylhalide per mole of the amine and the employment of such proportions is preferred.

It is preferred to employ polar solvents in carrying out this reaction. Representative solvents include, for example, acetonitrile, butanol, nitromethane and methyl ethyl ketone. When lower boiling solvents are employed, pressures higher than atmospheric may be necessary to permit the use of temperatures higher than the boiling point of the solvent. It is also within the scope of this invention to conduct the reaction in the absence of solvents provided that adequate control is maintained over the temperature.

Upon completion of the reaction, the product is removed from the reaction mixture. This separation can be achieved by (a) removing the solvent by evaporation under reduced pressure and recovering the product as a residue or (b) cooling the reaction mixture and mixing it with a solvent such as, for example, ethyl ether, hexane or mixtures thereof. If the product is solid, it can be separated by filtration or other known solid-liquid separation techniques; if the product is a liquid (oil), it can be separated by decantation or other conventional separation techniques. If desired, solid products can be further purified by recrystallization from solvents such as, for example, methyl ethyl ketone, ethyl acetate, ethyl ether, hexane, ethanol or mixtures thereof. The liquid products can sometimes be crystallized by trituration with the appropriate solvent.

While the above preparative procedures have been described wherein the product is in the form of the chloride or bromide salt (the benzylchloride or bromide having the starting reactant), other salts can be prepared employing conventional procedures.

Such additional salts are prepared by treating the chloride or bromide product at room temperature in water with the alkali or alkaline earth salt of the organic or inorganic acid from which the desired anion is derived. This salt is of the formula $$M^{\oplus}X^{\ominus}$$

wherein M represents the alkali metals such as sodium, potassium, lithium, cesium or rubidium, and the alkaline earth metals such as calcium, barium or strontium and X is as hereinabove set forth. These additional salts can also be prepared by passing the product bromide or chloride salt through an ion exchange column charged with the appropriate anion.

DESCRIPTION OF SOME PREFERRED EMBODIMENTS

The following examples illustrate the present invention and the manner by which it can be practical but, as such, should not be construed as limitations upon the overall scope of the same.

EXAMPLE I

N,N,N-tributyl-(3-methoxybenzyl)ammonium chloride

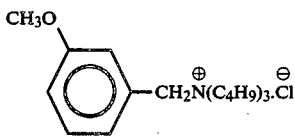

A mixture of 5.0 grams (0.03 mole) of 3-methoxybenzylchloride and 9.0 grams (0.048 mole) of tributylamine in 50 milliliters of acetonitrile was heated to reflux. The mixture was refluxed overnight and the solvent then removed by evaporation. The crude product which remained was mixed with ethyl ether. The product was recovered by filtration and dried. The tributyl-(3-methoxybenzyl)ammonium chloride was recovered, as a white powder, in a yield of 9.2 grams. The product melted at 161° C.–162° C. The structure of the compound was confirmed by NMR (Compound No. 1).

| Analysis: | % C | % H | % N |
|---|---|---|---|
| Calc. for $C_{20}H_{36}ClNO$: | 70.24 | 10.61 | 4.10 |
| Found: | 70.25 | 10.54 | 4.17 |

By following the preparative procedures as set forth in the above example and employing the appropriate starting reactants, the following compounds are prepared.

TABLE I $$Z\text{-}C_6H_4\text{-}CH_2\text{-}\overset{\oplus}{N}\text{-}(R)_3 \cdot A^{\ominus}$$

| Compound No. | Z | R | A$^{\ominus}$ | Melting Point |
|---|---|---|---|---|
| 2 | 3-MeO | Et | Cl | 181–182 |
| 3 | 4-MeO | Et | Cl | 129–131 |
| 4 | 3-MeO | n-Bu | Br | — |
| 5 | 4-MeO | n-Bu | Cl | 99–101 |
| 6 | 4-MeO | n-Bu | NO$_3$ | — |
| 7 | 3-MeS | Et | Cl | 202–203 |
| 8 | 4-MeS | Me | φSO$_3$ | — |
| 9 | 4-MeS | Et | Cl | 158–159 |
| 10 | 3-MeS | n-Bu | Cl | 133–134 |
| 11 | 4-MeS | n-Bu | Cl | 107–108 |
| 12 | 3-EtO | Me | SO$_4$ | — |
| 13 | 3-EtO | Et | Cl | 154–156 |
| 14 | 3-EtO | n-Bu | Cl | 140–142 |
| 15 | 3-EtS | Et | Cl | 141–143 |
| 16 | 3-EtS | n-Pr | I | — |
| 17 | 3-EtS | i-Pr | SCN | — |
| 18 | 3-EtS | n-Bu | Cl | 106–108 |
| 19 | 3-CH$_2$:CHO | Et | SCN | — |
| 20 | 3-CH$_2$:CHS | i-Bu | CH$_3$CO$_2$ | — |
| 21 | 3-n-PrO | Et | Cl | 166–167 |
| 22 | 3-n-PrO | Et | I | — |
| 23 | 3-n-PrO | Bu | Cl | 128–130 |
| 24 | 3-i-PrO | Et | Cl | 146–148 |
| 25 | 3-i-PrO | Bu | Cl | 135–136 |
| 26 | 4-n-PrO | Et | I | 85–87 |
| 27 | 4-n-PrO | Bu | Cl | 106–108 |
| 28 | 3-n-PrS | Me | C$_2$H$_5$CO$_2$ | — |
| 29 | 3-n-PrS | Et | Cl | 130–132 |
| 30 | 3-n-PrS | Bu | Cl | 91–92 |
| 31 | 4-i-PrS | Bu | PO$_4$ | — |
| 32 | 3-n-BuO | Et | Cl | 147–149 |
| 33 | 3-n-BuO | n-Bu | Cl | 112–113 |
| 34 | 4-n-BuO | Me | ClO$_3$ | — |
| 35 | 4-i-BuO | i-Bu | φSO$_3$ | — |
| 36 | 3-i-PentO | Et | Cl | 112–114 |
| 37 | 3-i-PentO | n-Bu | Cl | 116–117 |
| 38 | 3-n-HexO | Et | Cl | waxy solid |
| 39 | 4-n-HexS | n-Pr | Cl—φ-O | — |
| 40 | 3-n-HexO | n-Bu | Cl | waxy solid |

Me = methyl; Et = ethyl; Pr = propyl; Bu = Butyl; MeO = methoxy; MeS = methylthio; EtO = ethoxy; EtS = ethylthio; PrO = propoxy; PrS = propylthio; BuO = butoxy; PentO = pentoxy; HexO = hexyloxy and HexS = hexylthio.

It has been discovered that the compounds of the present invention can be employed as plant growth control agents for at least one of corn, wheat and sugar cane plants. In this capacity, the compounds of this invention or compositions containing these compounds, as the active ingredient, are useful in enhancing the growth of at least one of the above plants. The plants after treatment exhibit an increased plant weight.

PREPARATION OF STARTING MATERIALS

The alkoxy and alkylthio substituted benzylhalides employed as starting materials can be prepared employing conventional procedures. In one such procedure, an appropriate benzenemethanol is reacted with a halogenating agent such as hydrochloric or hydrobromic acid, thionyl chloride or bromide or N-bromosuccinamide in the presence of a solvent.

This reaction can be characterized as follows:

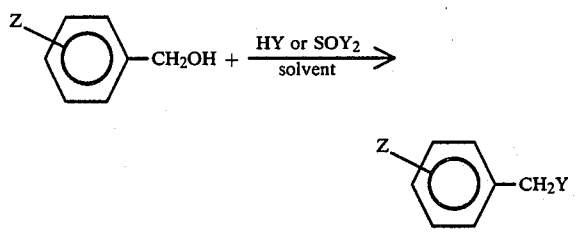

wherein Z and Y are as hereinabove defined.

In carrying out this reaction, the reactants and solvent are mixed together in any suitable fashion at room temperature. The reactants are maintained together until the reaction is complete, usually from a few minutes to 1 or more hours. The specific time period is dependent upon the specific reactants and solvents employed.

The amount of the reactants to be employed is not critical, some of the product being formed when employing any proportions. The reaction, however, consumes the reactants in the ratio of 1 mole of the benzyl alcohol per mole of the halogenating agent and the employment of such proportions is preferred.

It is preferred to employ polar solvents in carrying out this reaction. Representative solvents include, for example, acetonitrile, butanol, nitromethane and methyl ethyl ketone.

Upon completion of the reaction, the product is recovered from the reaction mixture employing conventional separation procedures.

The alkoxy and alkylthio substituted benzene methanols employed as starting materials are for the most part known and many are items of commerce. These compounds can be prepared employing a variety of procedures.

The alkoxy substituted benzenemethanols can be prepared by reacting a 3- or 4-alkoxy benzaldehyde with sodium borohydride in the presence of a solvent such as ethanol at temperatures below 50° C. This procedure is the one taught in German Offen. No. 2,757,031.

The alkylthio substituted benzenemethanols can be prepared by the reaction of a 3- or 4-bromobenzenemethanol and an appropriate sodium alkylmercaptide, alkylmercaptan or an alkyldisulfide in the presence of a solvent such as 2,4-lutidene or copper (I) bromide or cuprous oxide under reflux conditions for from about 5 to 48 hours or more. The reaction mixture is cooled and poured over concentrated hydrochloric acid and ice. The product is taken up in methylene chloride, filtered and the organic washed with dilute hydrochloric acid, then with diluted sodium bicarbonate and dried. The solvent is removed and the crude product which remains can be purified by distillation.

The compounds can be applied directly to the plant itself, i.e., aboveground surfaces of the plants, seeds, roots and the like.

The exposure of viable plants and plant parts to the action of a growth regulating amount of the compounds of the present invention is essential and critical for the practice of the present invention. The exact dosage to be employed is not the same for all plants with all compounds, and is dependent upon the response desired in the plant as well as such other factors as the plant species, and the stage of growth at which treatment is made, and climatic conditions such as temperature, wind and especially rainfall.

In foliar treatments for the enhancement of the growth of germinant seeds, emerging seedlings and established vegetation good results are obtained when from 0.002 pound to 5.0 pounds, preferably 0.01 to 2 pounds of the compounds are applied per acre.

The method of the present invention can be practiced by distributing the unmodified compounds upon the surfaces of the aboveground portion of plants. However, the present method also embraces the similar employment of liquid or dust compositions containing the compounds. In such usages, the compounds can be modified with one or a plurality of additaments or adjuvants including water or other liquid carriers, surface active dispersing agents and finely divided solids. Depending upon the concentration of the compounds, such augmented compositions are adapted to be distributed upon the aboveground surfaces of plants, or to be employed as concentrates and subsequently diluted with additional inert carrier to produce the ultimate treating compositions. In compositions where the adjuvant or helper is a finely divided solid, a surface active agent or the combination of a surface active agent and finely divided solid, and/or a liquid additament, the adjuvant and/or adjuvants cooperate with the compounds so as to facilitate the invention and obtain an improved and outstanding result.

As indicated above, the compound can be directly applied to seeds prior to planting. The application to seeds of an effective growth enhancing dosage of the active compounds is essential and critical for the practice of the present invention. Good results are obtained when the seeds are treated with the compounds at a dosage of from about 0.0001 pound per hundred pounds of seed up to the phytotoxic threshold. The latter is about 0.1 pound per hundred pounds of seed inasmuch as lasting phytotoxic effects are obtaining with many plants at dosage levels above the 0.1 pound level. Depending on the particular plant species and variety and on the growing conditions some undesirable phytotoxic effects may be encountered even below the 0.1 pound level. Within the above set forth treating range, the maximum growth enhancement response is obtained, and any phytotoxicity experienced in the very early stages of plant growth is usually overcome as the plant begins the growth and maturation habit which is characterized by the present process.

The treatment of the seeds may be accomplished by shaking or otherwise contacting the seeds with a dust composition containing the active agent, or by wetting the seeds with a liquid composition. In a convenient method of application, the compositions are applied in the form of dusts or sprays to the seeds as the latter are transported on the surface of a slowly moving belt or a perforated material such as a wire screen. In still another method, the required dosage of active agent can be applied on and about the seeds by the seed planting implement either in the hopper box or as the seeds are being planted into the soil or other growth media.

The exact concentration of the compounds to be employed in the treating compositions is not critical and may vary considerably provided the required dosage of the compounds is supplied upon the plant foliage. The concentration of the compound in liquid compositions employed to supply the desired dosage generally is from about 0.001 to 50 percent by weight although concentrations as low as 0.0001 percent and as high as 90 percent by weight are sometimes advantageously employed. In dusts, the concentration of toxicant is from about 0.1 to 90 percent by weight and usually not in excess of about 20 percent. In both liquid and dust compositions to be employed as concentrates, the compounds can be present in a concentration of from 5 to 98 percent by weight.

The quantity of treating compositions to be applied can vary considerably provided that the required dosage of the compound or active ingredient is applied in a sufficient amount of the finished composition to cover adequately the vegetation to be treated. In the treatment of seedlings good coverage is obtained when using from 1 to 60 gallons of finished spray composition per acre. Where large plants are concerned, it is frequently desirable to employ up to 600 gallons or more of the finished spray composition per acre to assure complete coverage of the aboveground portion of the vegetation. In the application of dusts to plant foliage, good results are obtained with from 40 to 2,000 pounds of finished dust per acre, the only requirement being that the required dosage be supplied in sufficient dust to achieve good coverage of the foliage.

Liquid compositions containing the desired amount of active ingredient can be prepared by dispersing the compounds in water or in organic liquid, with or without the aid of a suitable surface active dispersing agent such as an ionic or non-ionic emulsifying agent. Suitable organic liquid carriers include the agricultural spray oils and the petroleum distillates such as diesel fuel, kerosene, fuel oil and naphthas. The organic liquid compositions can contain a small amount of water as a solvent for the active ingredient. In such compositions, the carrier comprises an emulsion, namely, a mixture of water, emulsifying agent and organic liquid. In the liquid compositions, the choice of dispersing and emulsifying agent and the amount thereof employed is dictated by the nature of the composition and by the ability of the agent to facilitate the dispersion of the compounds in the carrier to produce the desired composition or to facilitate the wetting of surfaces upon which the compositions are applied. Dispersing and emulsifying agents which can be employed in the compositions include the condensation products of alkylene oxides with phenols and organic acids, alkyl aryl sulfonates, polyoxyalkylene derivatives or sorbitan esters, complex ether alcohols, mahogany soaps and the like.

In the preparation of dust compositions, the active ingredient is dispersed in and on a finely divided solid such as clay, talc, chalk, gypsum, sugar, salt, bicarbonate, fertilizer and the like. In such operations, the finely divided carrier is mechanically mixed or ground with the compounds. Similarly, dust compositions containing the compounds can be prepared from various of the solid surface active dispersing agents such as bentonite, fuller's earth, attapulgite and other clays. Depending upon the proportion of ingredients, these dust compositions can be employed as concentrates and subsequently diluted with additional solid surface active dispersing agent or with chalk, talc or gypsum, sugar, salts, fertilizer and the like to obtain the desired amount of active ingredient in a composition adapted to be employed for the modification of the growth of plants. Also such dust compositions can be dispersed in water with or without the aid of a dispersing agent to form spray mixtures.

When operating in accordance with the present invention, growth enhancing amounts of the compounds are dispersed in any convenient fashion. The application of spray and dust compositions to the aboveground surfaces of plants can be carried out by conventional methods, e.g., power dusters, boom and hand sprayers and spray dusters.

The expression "surface active dispersing agent" as herein employed is intended to include all agents which are capable of acting at the interfacial surface as the dispersion medium. Thus, the term is inclusive of the solid emulsifying agents such as finely divided aluminum hydroxide and finely divided bentonite, fuller's earth, attapulgite and other clays, as well as the ionic and non-ionic wetting and emulsifying agents such as the alkaline earth metal caseinates, alkyl aryl sulfonates, sulfonated oils, complex organic ester derivatives, complex ether alcohols and the like.

The finely divided inert solid or carrier as herein described refers to materials which are incapable of facilitating dispersion but which serve as a distribution medium for the active compounds. They include finely divided materials such as chalk, talc, gypsum, sugar, salts, bicarbonate, fertilizers and so forth.

EXAMPLE II

Tests were conducted to determine the effectiveness of various alkoxy and alkylthio substituted benzylammonium compounds in increasing the growth of corn as evidenced by an increase in the dry weight of corn plants.

Seeds of the corn variety Pioneer 3780 were planted in pots containing a mixture of soil and fertilizer. The seeded pots were maintained under normal greenhouse conditions. Two weeks after the planting, the plants were at the 2-3 leaf stage. At this time, the plants were sprayed to run-off with various dilutions of the benzylammonium compounds. The solutions were prepared by dissolving a predetermined amount of one of the compounds in a predetermined amount of water containing 0.1 percent of a wetting agent. There were 10 replications at each concentration of each compound and a set of untreated plants were maintained as controls.

After treatment, the plants were maintained under greenhouse conditions conducive to good plant growth. At the end of this period, the plants were cut off at the soil line and placed in a forced air oven at 100° C. for 48 hours. The dry weight of the plants was measured and the results calculated as a percent of control. These results, the compounds employed and the amounts employed are set forth below in Table II.

TABLE II

| Compound No. | Treating Rate in ppm | Dry Weight of Indicated Plants as Percent Increase Over the Weight of Control Plants |
|---|---|---|
| 1 | 6.0 | 13.0 |
|   | 25.0 | 9.0 |
|   | 100.0 | 14.0 |
|   | 200.0 | 4.0 |
| 2 | 10.0 | 7.0 |
|   | 100.0 | 7.0 |
| 3 | 100.0 | 1.0 |
| 5 | 200.0 | 12.0 |
|   | 400.0 | 3.0 |
| 7 | 10.0 | 11.0 |

TABLE II-continued

| Compound No. | Treating Rate in ppm | Dry Weight of Indicated Plants as Percent Increase Over the Weight of Control Plants |
|---|---|---|
|  | 100.0 | 13.0 |
| 23 | 10.0 | 19.0 |
|  | 100.0 | 9.0 |
| 24 | 10.0 | 9.0 |
|  | 100.0 | 15.0 |
| 33 | 10.0 | 54.0 |
|  | 100.0 | 32.0 |
| 36 | 10.0 | 11.0 |
|  | 100.0 | 10.0 |
| 37 | 10.0 | 87.0 |
|  | 100.0 | 67.0 |
| 38 | 10.0 | 15.0 |
|  | 100.0 | 10.0 |

What is claimed is:

1. A method for enhancing the growth of corn, wheat and sugar cane plants to obtain an increase in weight of said plants which comprises contacting plants or plant parts or their habitat with a growth enhancing amount of a composition containing an inert carrier and as the active material a compound corresponding to the formula

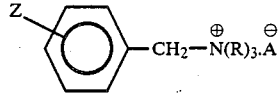

wherein:
Z represents in the 3 or 4 ring position, $C_1$–$C_6$ alkoxy or $C_1$–$C_6$ alkylthio;
each R independently represents $C_1$–$C_4$ alkyl with the proviso that when Z is a $C_6$ alkoxy or $C_6$ alkylthio, R cannot be $C_4$ alkyl; and
A represents a non-phytotoxic anion.

2. A method as defined in claim 1 wherein Z is $C_1$–$C_6$ alkoxy.

3. The composition as defined in claim 2 wherein the active material is N,N,N-tri-n-butyl-(3-n-butoxybenzyl)ammonium chloride.

4. The composition as defined in claim 2 wherein the active material is N,N,N-tri-n-butyl-(3-i-pentoxybenzyl)ammonium chloride.

5. The composition as defined in claim 1 wherein Z is alkylthio.

6. The method as defined in claim 1 in which plant seeds are contacted.

7. The method as defined in claim 6 wherein the seeds are contacted with from 0.0001 to 0.1 pound of the active material per 100 pounds of seed.

8. The method as defined in claim 1 in which the aboveground portions of the plants are contacted.

9. The method as defined in claim 8 wherein the aboveground portions of the plants are contacted with from 0.002 pound to 5.0 pounds of the active material per acre.